United States Patent [19]

Kanegae et al.

[11] Patent Number: 4,810,509

[45] Date of Patent: Mar. 7, 1989

[54] METHOD FOR PRODUCING YEAST EXTRACT

[75] Inventors: Yukihiro Kanegae, Kobe; Yoshio Sugiyama; Kanshiro Minami, both of Takasago, all of Japan

[73] Assignee: Takeda Chemical Industries, Ltd., Osaka, Japan

[21] Appl. No.: 60,085

[22] Filed: Jun. 9, 1987

[30] Foreign Application Priority Data

Jun. 9, 1986 [JP] Japan .................................. 61-133135

[51] Int. Cl.$^4$ ............................................... A23J 1/18
[52] U.S. Cl. ...................................... 426/60; 426/62; 426/656; 426/650
[58] Field of Search ................... 426/7, 60, 61, 62, 656, 426/650

[56] References Cited

U.S. PATENT DOCUMENTS

| 3,720,585 | 3/1973 | Tannenbaum et al. | 195/98 |
| 4,135,000 | 1/1979 | Schuldt | 426/60 |
| 4,264,628 | 4/1981 | Hill | 426/60 |

FOREIGN PATENT DOCUMENTS

| 37799 | 9/1981 | Japan . |
| 109153 | 6/1984 | Japan . |

*Primary Examiner*—Marianne Cintins
*Attorney, Agent, or Firm*—Wenderoth, Lind & Ponack

[57] ABSTRACT

A tasty yeast extract is obtained by heating an aqueous suspension of yeast at 55° to 70° C., allowing the yeast cells to autolyze at pH 8 to 10, and eliminating water insoluble matter from the suspension and recovering the yeast extract.

12 Claims, No Drawings

METHOD FOR PRODUCING YEAST EXTRACT

BACKGROUND OF THE INVENTION

This invention relates to a tasty yeast extract and its production.

Conventionally yeast extract has been produced by an autolytic method in which yeast cells are allowed to autolyze or by a hydrolytic method in which yeast cells are hydrolyzed with acid, alkali or hydrolase. The autolytic method generally comprises hydrolysis of yeast cells by the enzymes present within the yeast cells in the presence of a so-called accelerator such as an organic solvent (e.g. toluene and ethyl acetate) and common salt. However the conventional methods do not attempt to effectively utilize the ribonucleic acid present in yeast cells, so that ribonucleic acid is mostly decomposed into non-tasty compounds and thus tasty 5'-ribonucleotide is hardly found in the product.

As for the hydrolysis of yeast cells with hydrolase, a method is known in which an extract of ribonucleic acid obtained by treatment of yeast cells with an alkali or common salt, or yeast cells themselves are treated with a nuclease derived from microorganisms, animals, or plants, so that ribonucleic acid may be utilized as 5'-ribonucleotide (Japanese patent application Laid-Open No. 109153/84). However such a method is disadvantageous because the addition of enzymes derived from other species of organisms is required which makes the process complicated and less economical.

On the other hand, methods for extraction and elimination of ribonucleic acid in cells of microorganisms have been developed for utilization of microbial protein as a foodstuff or feed. A method is known in which a specified yeast of genus Candida is heated for a short time, i.e. at 60° to 70° C. for 5 to 20 seconds, followed by warming at 45° to 50° C. at pH 4.5 to 7.0 for about 20 minutes (U.S. Pat. No. 3,720,585). However, by this method ribonucleic acid is decomposed into non-tasty 3'-ribonucleotide, therefore this method is not appropriate for production of yeast extract. Another method is also known for production of microbial protein with a low content of nucleic acid in which cells are heated at 63° to 67° C. at pH 7 to 8.5 for 20 minutes to 20 hours so that ribonucleic acid may be decomposed to give 5'-ribonucleotide (Japanese Examined patent application No. 37799/81). However, because the enzymes required for autolysis may be inactivated by the conditions of treatment, this method is also inappropriate for production of yeast extract.

The method of production of yeast extract by autolysis is desirable for production of natural seasonings because it makes use of the action of enzymes present in the starting material yeast. However, as described above, the extract obtained by the conventional procedures of autolysis has an unsatisfactory taste with respect to body or flavor, because not only does the extract contain a 5'-ribonucleotide content of 0.5% at best and usually less than 0.1%, but the content of other tasty ingredients is also low. Hence, a satisfactory method for the production of a tasty yeast extract has not been available.

SUMMARY OF THE INVENTION

Under the circumstances described above, the inventors completed this invention as a result of their search for a practical and advantageous procedure for the production of a tasty yeast extract by the autolytic method.

That is, this invention relates to a process for the production of a yeast extract, which comprises heating an aqueous suspension of edible yeast at 55° to 70° C., autolyzing the yeast cells at pH 8 to 10, water insoluble matter from the suspension and recovering the yeast extract.

The yeast extract in this invention contains 5'-purine nucleotides, and such 5'-purine nucleotides are those containing one or more of 5'-guanylic acid, 5'-adenylic acid, and 5'-inosinic acid.

DESCRIPTION OF THE PREFERRED EMBODIMENTS

In this invention the starting material may be any kind of yeast so long as it is edible, for example yeast belonging to genera of Saccharomyces, Candida, and Kluyveromyces. Yeast belonging to Saccharomyces includes bakers' yeast, brewers' yeast, sake-brewers' yeast, and wine-brewers' yeast, e.g. seed strains of *Saccharomyces cerevisiae* [e.g. *Saccharomyces cerevisiae* B No. 21 IFO 2133 (FERM P-8799) strain], seed strains of *Saccharomyces rouxii* (e.g. IFO 0495 strain), and seed strains of *Saccharomyces uvarum* (e.g. IFO 0751). Yeast belonging to Candida genus is exemplified by seed strains of *Candida utilis* (e.g. IFO 0619, IFO 0639, IFO 0626 strains), and that belonging to Kluyveromyces genus is exemplified by seed strains of *Kluyveromyces fragilis* (e.g. IFO 0541) and seed strains of *Kluyveromyces lactis* (e.g. IFO 0648).

The IFO numbers described above are the deposition numbers in Institute For Fermentation, OSAKA (IFO), and these strains are listed in the List of Cultures published by the Institute. The FERM P numbers are the deposition numbers in the Fermentation Research Institute, Agency of Industrial Science and Technology, Ministry of International Trade and Industry, Japan (FRI).

Among the above microorganisms, *Saccharomyces cerevisiae* B. No. 21 IFO 2133 was also deposited on June 6, 1986 at FRI under the accession number of FERM P-8799 and, the deposit being converted to a deposit under the Budapest Treaty, has been stored at FRI under the accession number of FERM BP-1349.

It is desirable for the strain of Candida genus used in this invention as a starting material to be sensitive to 5-fluorouracil (5-FU), because a product of yeast extract with a higher content of 5'-purine nucleotide is obtained.

Such yeasts of Candida genus which are sensitive to 5-FU are those whose growth is not observed or extremely slow in a medium containing 5-FU. It is particularly preferable that the growth inhibitory concentration of 5-FU be 1/5 or less that of their parent strains.

The sensitivity to 5-FU is defined as follows: A platinum loop amount of edible yeast taken from the slant culture is inoculated into a test tube containing 5 ml of Medium B shown in Table 5 (see Example 3), and subjected to shaking culture at 28° C. for 24 hours, 0.02 ml of which is transferred to medium B to which 5-FU has been added to various concentrations, and incubated at 28° C. for 48 hours. The culture is diluted 20 times with water and the absorbance at 590 m$\mu$ (OD$_{590}$) is measured with, for a Coleman Junior Spectrophotometer. The minimum concentration of 5-FU at which the absorbance is 0.075 or less is determined as the growth inhibitory concentration. The above defined growth inhibitory concentration of a parent strain is determined, and according to principles of mutation the mutants showing a 5-fold or more lower growth inhibitory concentration than the value of the parent strain are derived as 5-FU sensitive strains. The preferable growth inhibitory concentration of 5-FU sensitive strains is about 0.5 mg/l or less in the liquid Medium B. Such 5-FU sensitive strains can be obtained by the so-called replica-plating method comprising treatment of yeasts of Candida genus as mentioned above by X-ray or ultraviolet ray, or with an agent such as N-methyl-N'-nitro-N-nitrosoguanidine, followed by selection of strains that do not grow on agar Medium B to which 5-FU has been added. Such 5-FU sensitive strains include *Candida utilis* F-64 (IFO 10209, FERM P-8798) which is described in Example 3. This microorganism was deposited on June 6, 1986 at FRI under the above accession number, the deposit of which was converted to a deposit under the Budapest Treaty, and has been stored at FRI under the accession number of FERM BP-1348.

In this invention, the yeast starting material described above is cultured in a nutrient medium containing a carbon source, nitrogen source, a inorganic salts, etc. The cells are separated, for example, by centrifugation, and washed with water appropriately, and the resulting live yeast cells are used for production of the yeast extract of this invention. The yeast cells are suspended in water at the concentration of preferably about 5 to 15% on a dry weight basis and heated at 55° to 70° C., preferably 60° to 65° C. Generally it is desirable to heat the yeast for 5 to 20 seconds. This treatment is supposed to crack the cell wall of the yeast and induce autolysis. Treatment at below 60° C. or treatment for a too short a period tends to result in insufficient autolysis in the next process. Treatment at over 70° C. or treatment for a too long period, for example for 30 seconds or more, is undesirable, because proteases involved in autolysis will be inactivated, which results in a low yield of yeast extract. A heat exchanger is usually used for this heat treatment because it enables uniform heating in a short period and rapid cooling after heating.

The yeast cells after heat treatment are then allowed to autolyze at pH 8 to 10, preferably pH 8.5 to 9.5. The pH may be adjusted before heat treatment, but generally it is desirable to adjust after heat treatment. Agents used for pH adjustment are not specified so long as they are edible alkalis, but sodium hydroxide and potassium hydroxide are preferably used. Then the yeast suspension in water is kept to about 35° to 50° C., preferably at 40° to 45° C., for about 4 to 10 hours, at which time the enzymes relating to autolysis promote autolysis while 5'-purine nucleotides are produced by the action of nucleases. At a pH more acidic than the range described above, non-tasty 3'-purine nucleotides are produced so that tasty yeast extract cannot be obtained. By adjusting pH in the range specified in this invention, 5'-purine nucleotides and other extract ingredients (peptides, amino acids, sugars, etc.) are solubilized in good yields. With the increase of temperature of autolysis over 50° C., the amount of 5'-purine nucleotides obtained decreases, so that a tasty extract of good quality becomes difficult to obtain, whereas at a temperature below 35° C. autolysis can be inactivated. When autolysis is allowed to occur for about 4 to 10 hours, the extract is tasty and is obtained in good yield. In this way, 5'-purine nucleotides (e.g. 5'-adenylic acid and 5'-guanylic acid) derived from yeast cells can be obtained in a solubilized state in good yield.

After the treatment described above, water insoluble matter is removed by routine methods, and the resultant solution containing the extract ingredients is collected. Here a method for removal of insoluble matter is preferably employed in which the pH of the reaction mixture after autolysis is adjusted to 5 to 7, followed by heating at about 90° C. or more for about 5 to 10 minutes and then centrifugation, filtration, etc. Thus a yeast extract containing 5'-purine nucleotides and other water-soluble ingredients (e.g. amino acids, peptides, sugars) is obtained. This yeast extract produced by this method contains a 1% or more content, and usually about a 1.5 to 10% content of 5'-purine nucleotides on a dry weight basis. The solution containing the extract ingredients, after treatments such as decolorization and deodorization, if necessary, is processed into liquid, paste, or powder products according to the purposes for which it is used.

In this invention, in an appropriate process after autolysis, treatment with 5'-adenylate deaminase can convert 5'-adenylic acid in the extract into 5'-inosinic acid which is tastier. The 5'-adenylate deaminase used may be the one produced by *Penicillium citrinum* or the one produced by microorganisms belonging to genus Aspergillus. For example, commercially available 5'-adenylate deaminase (Deamizyme Product of Amano Pharmaceutical Co., Japan, $5 \times 10^4$ unit) can be used, which is sufficient for this purpose when used to about 0.05 to 0.5 g per 1 g of 5'-adenylic acid. The amount of other preparations of 5'-adenylate deaminase to use is determined appropriately on the basis of the enzymatic activity etc. The reaction with 5'-adenylate deaminase is conducted at pH about 4 to 6.5, at about 30°-55° C., usually for 2 hours or more, preferably for 2-5 hours.

According to the method of production of this invention, a tasty yeast extract is obtainable by autolysis of yeast cells. This method is very desirable for production of natural seasoning agents in that it requires no autolysis-accelerator during autolysis and in that a yeast extract rich in 5'-purine nucleotides is obtainable without treatment with a protease or 5'-phosphodiesterase. This yeast extract may be used widely for cooking and as a seasoning agent for various processed foods.

In the following, this invention is explained in in further detail.

EXPERIMENTAL EXAMPLE 1

Two liters of a medium containing 100 g of spent molasses (assumed to consist of total sugar), 2.5 g of monopotassium phosphate, 0.5 g of magnesium sulfate, 2.5 g of urea and 2 g of yeast extract (manufactured by Daigo Nutritive Chemicals Co., Japan) per 1 liter of the medium was put into a 5 l jar-fermentor and sterilized at 121° C. for 15 minutes. To this fermentor, 100 ml of *Candida utilis* IFO 0626 obtained by shaking culture in the seed medium shown in Table 1 in a flask at 28° C. for 20 hours was transferred, which was incubated under aeration at 1 l/min, with stirring at 800 rpm, at 28° C. for 15 hours. The yeast cells obtained by centrifugation of the culture was washed with water once, to which water was added to prepare 480 ml of a yeast slurry of about 100 mg/ml on a dry weight basis. Fifty ml of this slurry was heated by allowing it to pass at a transit time of 10 seconds through a stainless tube of 2 mm internal diameter set in a thermostat (water bath) at 55° C., and then cooled immediately. Heating was also carried out separately at 60° C., 65° C., and 70° C. Then the slurry was kept in a thermostat at 40° C. for 4 hours while the pH was maintained at 9.0 by dropwise addition of 1 N-NaOH so that autolysis might occur, followed by adjustment of pH to 6.0 with 2 N-HCl and boiling for 5 minutes. Then the autolysate was centrifuged and the precipitate was washed with water, to give 100 ml of supernatant combined with the washing.

The slurry was heated at 60° C. for 5, 10, or 20 seconds, and allowed to react at 40° C. at pH 9.0 for 4 hours. Then, the autolysate was neutralized, boiled and centrifuged in the same way as described above, and the resultant precipitate was washed once, to give 100 ml of supernatant combined with the washing. These supernatant preparations were analyzed for 5'-purine nucleotide content with a high performance liquid chromatograph filled with Hitachi Gel #3013N.

The mobile phase used was a buffer containing 0.06M $NH_4Cl$, 0.01M $KH_2PO_4$, 0.01M $K_2HPO_4$, and 4% $CH_3CN$. The 5'-purine nucleotide content in the supernatant obtained by boiling for 5 minutes the yeast slurry followed by centrifugation was determined and expressed as free 5'-purine nucleotide content. As shown in Table 2, free 5'-purine nucleotide content which had been 13.4 mg of 5'-adenylic acid and 3.3 mg of 5'-guanylic acid increased in all of the supernatant preparations. The amounts extracted of both ribonucleotides were the largest at 60° C. and treatment for 10 seconds was the most desirable.

TABLE 1

| (Medium A) | |
|---|---|
| | per litter |
| glucose | 50 g |
| $KH_2PO_4$ | 4 g |
| KCl | 1 g |
| $MgSO_4.7H_2O$ | 0.7 g |
| $FeSO_4.7H_2O$ | 0.2 g |
| $(NH_4)_2SO_4$ | 2 g |
| $(NH_2)_2CO$ | 4 g |
| $CaCl_2.2H_2O$ | 0.15 g |
| NaCl | 0.1 g |
| $ZnSO_4.7H_2O$ | 0.02 g |
| $MnSO_4.nH_2O$ | 0.01 g |
| $CuSO_4.5H_2O$ | 0.25 mg |
| Yeast extract | 2 g |

TABLE 2

| (Conditions of heat treatment) | | | | |
|---|---|---|---|---|
| heating conditions | | dry | | |
| temp. (°C.) | time (sec.) | weight (g) | 5'-adenylic acid* (mg) | 5'-guanylic acid* (mg) |
| 55 | 10 | 1.93 | 25.2 | 13.0 |
| 60 | 10 | 1.81 | 34.1 | 27.2 |
| 65 | 10 | 1.65 | 32.7 | 22.3 |
| 70 | 10 | 1.63 | 21.2 | 11.0 |
| 60 | 5 | 1.76 | 33.4 | 17.0 |
| 60 | 10 | 1.66 | 34.6 | 26.2 |
| 60 | 20 | 1.71 | 23.7 | 15.2 |
| free 5'-purine nucleotide** | | | 13.4 | 3.3 |

*expressed as a free acid content
**5'-purine nucleotide content in the supernatant obtained by boiling of yeast slurry at 100° C. for 5 minutes followed by cooling and centrifugation.

EXPERIMENTAL EXAMPLE 2

In the same way as described in Experimental Example 1, Candida utilis IFO 0626 was cultured, and then a yeast slurry of about 100 mg/ml was prepared. This slurry was heated at 60° C. for 10 seconds by the heat exchange method as described above. Fifty ml each of the slurry thus treated was kept in a water bath at 35°, 40°, 45°, 50°, or 55° C., at pH 9.0 for 4 hours, neutralized and boiled as described above, to give 100 ml each of supernatant preparation.

Similarly 50 ml each of the slurry after heat treatment was kept in a water bath at 40° C. at pH 8.0, 8.5, 9.0, or 9,.5 for 4 hours so that autolysis might occur, neutralized and boiled, to give 100 ml each of supernatant preparation. The content of 5'-purine nucleotide in these supernatant preparations was determined with a high performance liquid chromatograph and the results are shown in Table 3. The results showed that the optimal reaction temperature is 35° to 50° C., particularly 40° to 45° C., and the optimal reaction pH is about 9.

With an increase of temperature the dry weight of the extract increased, although the yield of 5'-adenylic acid and that of 5'-guanylic acid decreased gradually with increase of temperature over 40° C., and at 55° C. the decomposition of nucleic acids was remarkably inhibited.

TABLE 3

| Reaction conditions of autolysis | | | | |
|---|---|---|---|---|
| reaction conditions | | dry weight (g) | 5'-adenylic acid* (mg) | 5'-guanylic acid* (mg) |
| pH | temp. (°C.) | | | |
| 9.0 | 35 | 1.32 | 21.6 | 19.5 |
| 9.0 | 40 | 1.59 | 30.8 | 30.0 |
| 9.0 | 45 | 1.65 | 28.6 | 24.8 |
| 9.0 | 50 | 1.82 | 24.5 | 12.5 |
| 9.0 | 55 | 1.93 | 19.4 | 5.7 |
| 8.0 | 40 | 1.39 | 23.8 | 22.4 |
| 8.5 | 40 | 1.45 | 26.6 | 24.8 |
| 9.0 | 40 | 1.62 | 32.1 | 30.3 |
| 9.5 | 40 | 1.73 | 30.2 | 29.0 |
| free 5'-purine nucleotide** | | | 12.3 | 3.4 |

*expressed as a free acid content
**means the same as described in Table 2

EXAMPLE 1

Candida utilis IFO 0626 was cultured in the same way as described in Experimental Example 1, and then 460 ml of yeast slurry of 102 mg/ml was prepared. This slurry was heated at 60° C. for 10 seconds by the heat exchange method as described above. The resultant liquid was kept in a water bath at 40° C. and the pH was adjusted to and kept at 9.0 with 1 N-NaOH for 6 hours so that autolysis might occur. After the reaction, pH was adjusted to 6.0 with 2 N-HCl and the reaction mixture was boiled for 5 minutes, followed by cooling and centrifugation. The precipitate was washed with water and 800 ml of the supernatant combined with the washings was obtained. The extract thus obtained contained 15.5 g of solid matter, and the content of 5'-adenylic acid and that of 5'-guanylic acid were 1.9% and 1.5%, respectively, on a solid matter basis. A concentrate of the extract to 150 ml was found to be an excellent, full-bodied and tasty extract.

EXAMPLE 2

Three strains of yeast, Candida utilis IFO 0619, Candida utilis IFO 0626 and Candida utilis IFO 0639, were cultured in the seed medium listed in Table 1, respectively and each main culture was carried out in a 5 l jar fermentor in the same way as described in Experimental Example 1. Cells were collected from the resultant culture, and washed with water twice. From the cells of each strain, 450, 490, and 480 ml of yeast slurry preparations of 100 mg/ml on a dry weight basis were obtained. Two hundred ml each of the slurry was heated at 60° C. for 10 seconds, and allowed to autolyze by keeping at pH 9.0 at 40° C. for 6 hours. After the pH was adjusted to 6 with 2 N-HCl, the slurry was boiled for 5 minutes and then centrifuged. The precipitate was washed with water once, and 400 ml of supernatant combined with the washing was obtained. The content of 5'-purine nucleotide in the supernatant was analyzed with a high performance liquid chromatograph, and the results are shown in Table 4. All of the extracts were found to be rich in 5'-purine nucleotide.

TABLE 4

| Strains | weight of dried matter | 5'-adenylic acid (mg) | 5'-guanylic acid (mg) |
|---|---|---|---|
| Candida utilis IFO 0619 | 5.68 | 70.2 | 33.6 |
| Candida utilis IFO 0639 | 6.34 | 59.4 | 19.2 |
| Candida utilis IFO 0626 | 6.02 | 123 | 76.8 |

EXAMPLE 3

(1) Derivation of 5-fluorouracil sensitive mutants

Candida utilis IFO 0626 was shaking-cultured in the liquid medium shown in Table 5 at 28° C. for 16 hours, and the cells were collected from the culture. The cells were suspended in 0.1M Tris-maleate buffer (pH 8.0), to which N-methyl-N'-nitro-N-nitrosoguanidine was added to the final concentration of 200 μg/ml, and kept at 28° C. for 30 minutes. Then the suspension was applied onto the medium shown in Table 5 containing 2% agar. The resulting colonies were replica-plated onto the agar medium described above to which 1.0 mg/ml of 5-fluorouracil had been added, and the strain that did not grow, F-64 strain (IFO 10209, FERM BP-1348), was collected. The growth of this strain and the parent strain in the 5-FU containing medium is shown in Table 6.

TABLE 5

| (Medium B) | |
|---|---|
| | g per l of the medium |
| KH$_2$PO$_4$ | 2.0 |
| (NH$_4$)$_2$SO$_4$ | 3.0 |
| MgSO$_4$.7H$_2$O | 1.0 |
| polypeptone | 3.5 |
| Yeast extract | 4.0 |
| glucose | 20.0 |

TABLE 6

| (Growth inhibitory concentration of 5-FU) | | |
|---|---|---|
| 5-FU (mg/ml) | IFO 0626 strain | F-64 strain |
| 0 | 0.460 | 0.440 |
| 0.1 | 0.455 | 0.405 |
| 0.5 | 0.450 | 0.075 |
| 1.0 | 0.390 | 0.055 |
| 2.0 | 0.152 | 0.060 |
| 3.0 | 0.075 | 0.050 |
| 5.0 | 0.050 | 0.055 |

OD$_{590}$ mm (× 20)

(2) Production of extract from 5-fluorouracil sensitive cells

F-64 Strain was cultured in the seed medium shown in Table 1, and main culture was carried out in a 5 l jar fermentor in the same way as described in Experimental Example 1. Cells were collected from the culture and washed with water twice. Water was added to these yeast cells to prepare 485 ml of yeast slurry of 98 mg/ml on a dry weight basis. After heat treatment at 60° C. for 10 seconds, the slurry was kept in a water bath at 40° C. and allowed to autolyze at pH 9.0 adjusted with 1 N-NaOH for 4 hours. When autolysis completed, the autolysate was adjusted to pH 6.0 with 2 N-HCl, boiled for 5 minutes, cooled and centrifuged. The precipitate was washed with water once and 800 ml of supernatant combined with the washing was obtained. Solid matter in this extract weighed 15.3 g, and 5'-adenylic acid and 5'-guanylic acid accounted for 3.1% and 2.2%, respectively, of the solid matter.

EXAMPLE 4

Two liters of a medium which contained 20 g of spent molasses which was assumed to be total sugar, 2.5 g of monopotassium phosphate, 0.5 g of magnesium sulfate, 2.5 g of urea, and 2 g of yeast extract (manufactured by Daigo Nutritive Chemical Co.) per l of the medium was placed into a 5 jar fermentor and sterilized at 121° C. for 15 minutes. To this medium 100 ml of the culture of Saccharomyces cerevisiae B No. 21 IFO 2133 (FERM BP-1349) which had been obtained by shaking culture in a flask in the seed medium shown in Table 5 at 28° C. for 20 hours was transferred and cultured. From 10 hours after the beginning of culture, spent molasses were continuously added at the rate of 15 g per 1 hour. Cells were collected from 2350 ml of 16 hour-culture by centrifugation, washed with water once, and used for preparation of 460 ml of yeast slurry of 101 mg/ml on a dry weight basis. This slurry was heated at 65° C. for 10 seconds, and allowed to autolyze by keeping it at pH 9.0 at 40° C. or 6 hours. Then the slurry was adjusted to pH 6.0 with 2 N-HCl, boiled for 5 minutes, and centrifuged. The precipitate obtained was washed with water once, and 600 ml of supernatant combined with the washing was obtained. This extract contained 15.1 g of solid matter, and 5'-adenylic acid and 5'-guanylic acid accounted for 1.4% and 0.2%, respectively, of the solid matter. The concentrate of the extract to 150 ml was found in a sensory test to be excellent, full-bodied and tasty.

EXAMPLE 5

F-64 Strain obtained in Example 3 was cultured in a 5 l jar fermentor in the same way as described in Example 3, and 465 ml of yeast slurry of 101 mg/ml was prepared. This slurry was heated at 60° C. for 10 seconds, and allowed to autolyze by keeping it at pH 9.0 with 2 N-NaOH at 40° C. for 6 hours. Then the slurry was adjusted to pH 6.0 with 2 -N-HCl, boiled for 5 minutes, and centrifuged. The precipitate was washed with water once, and 800 ml of supernatant combined with the washing was obtained. To the extract 30 mg of 5'-adenylate deaminase (Deamizyme, manufactured by Amano Pharmaceutical Co., Japan) was added and kept at 50° C. for 6 hours. The reaction mixture was again boiled for 5 minutes, concentrated to 150 ml, and dried under reduced pressure. This powdered yeast extract contained 14 g of solid matter, and 5'-inosinic acid and 5'-guanylic acid accounted for 3.2% and 2.1%, respectively, of the solid matter. This extract was found in a sensory test to be excellent, full-bodied and tasty.

What we claim is:

1. A method for producing yeast extract, which comprises (1) heating an aqueous suspension of edible yeast at 55° to 70° C., (2) allowing yeast cells in the suspension to autolyze at pH 8 to 10, (3) adjusting the pH of the autolyzed yeast suspension to 5 to 7, (4) heating the suspension at 90° C. or more, (5) eliminating water-insoluble matter from the thus heated suspension and (6) recovering the yeast extract.

2. The method according to claim 1, wherein the yeast belongs to the genus Saccharomyces.

3. The method according to claim 1, wherein the yeast belongs to *Saccharomyces cerevisiae*.

4. The method according to claim 1, wherein the yeast belongs to the genus Candida.

5. The method according to claim 1, wherein the yeast belongs to *Candida utilis*.

6. The method according to claim 1, wherein the yeast belongs to the genus Candida whose growth is not observed substantially in a liquid medium containing about 0.5 mg/l or less of 5-fluorouracil.

7. The method according to claim 6, wherein the yeast belongs to *Candida utilis*.

8. The method according to claim 6, wherein the yeast is *Candida utilis* F-64 (IFO 10209, FERM BP-1348).

9. The method according to claim 1, wherein the aqueous suspension before autolysis is heated for 5 to 20 seconds with a heat exchanger.

10. The method according to claim 1, wherein the autolysis is carried out at pH 8.5 to 9.5.

11. The method according to claim 1, wherein the autolysis is carried out at about 35° to 50° C. for about 4 to 10 hours.

12. The method according to claim 1, wherein after autolysis the autolyzate is treated with 5'-adenylate deaminase to convert 5'-adenylic acid to 5'-inosinic acid.

* * * * *